United States Patent [19]

Pawson

[11] 4,132,723

[45] Jan. 2, 1979

[54] SUBSTITUTED PHENYL- OR CYCLOHEX-1-EN-1-yl-3,7-DEMETHYL-NONA-2,4,6-TRIENOIC ACIDS AND DERIVATIVES THEREOF

[75] Inventor: Beverly A. Pawson, Montclair, N.J.

[73] Assignee: Hoffmann-La Roche Inc., Nutley, N.J.

[21] Appl. No.: 771,273

[22] Filed: Feb. 23, 1977

Related U.S. Application Data

[63] Continuation of Ser. No. 495,482, Aug. 7, 1974, abandoned.

[30] Foreign Application Priority Data

Jul. 16, 1974 [CH] Switzerland ..................... 9704/74
Aug. 24, 1973 [CH] Switzerland ..................... 12197/73

[51] Int. Cl.$^2$ .......................... C09F 5/00; C11C 3/00
[52] U.S. Cl. .................................... 260/404; 260/408; 260/413; 260/405; 260/326.2; 260/410.9 R; 544/58; 544/171; 546/193; 546/189; 546/208; 546/262; 546/281; 546/247; 546/248; 546/335; 546/341; 546/344

[58] Field of Search ................. 260/410.9 R, 410.9 V, 260/410.9 M, 413 L, 404, 405, 408, 326.2, 295 R, 293.88; 544/58, 171

[56] References Cited

FOREIGN PATENT DOCUMENTS 950552 10/1956 Fed. Rep. of Germany.

OTHER PUBLICATIONS

Chemical Abstracts, vol. 74, No. 124946k.
Chemical Abstracts, vol. 8, No. 106498b.

Primary Examiner—John Niebling
Attorney, Agent, or Firm—Jon S. Saxe; Bernard S. Leon; George W. Johnston

[57] ABSTRACT

Novel 9-substituted phenyl- or cyclohex-1-en-1-yl-3,7-dimethyl-nona-2,4,6-trienoic acids or derivatives thereof, -trienal or -trienol derivatives are described. The subject compounds are useful in the treatment of neoplasias, certain dermatoses and inflammatory and allergic dermatological conditions.

5 Claims, No Drawings

SUBSTITUTED PHENYL- OR CYCLOHEX-1-EN-1-yl-3,7-DEMETHYL-NONA-2,4,6-TRIENOIC ACIDS AND DERIVATIVES THEREOF

This is a continuation of application Ser. No. 495,482 filed August 7, 1974, entitled "POLYENE COMPOUNDS" now abandoned.

DETAILED DESCRIPTION OF THE INVENTION

The present invention pertains to compounds represented by the formula

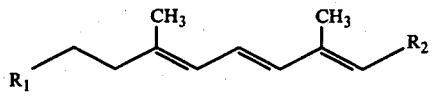

wherein $R_1$ is a 2,6,6-trimethyl-cyclohex-1-en-1-yl group or a phenyl group which is substituted in positions 2 and 6 by a member selected from the group consisting of halogen, lower alkyl and lower alkoxy and in at least one of positions 3, 4 and 5 by a member selected from the group consisting of halogen, hydroxy, lower alkyl, lower alkenyl, lower alkoxy, lower alkenoxy, lower alkanoyloxy, nitro, amino, mono(lower alkyl)amino, di(lower alkyl)amino, lower alkanoylamido and a nitrogen-containing heterocyclic group; and $R_2$ is selected from the group consisting of formyl, hydroxymethyl, alkoxymethyl, alkanoyloxymethyl, carboxyl, alkoxycarbonyl, alkenoxycarbonyl, alkynoxycarbonyl, carbamoyl, mono(lower alkyl) carbamoyl, di(lower alkyl)carbamoyl and a nitrogen-containing heterocycle-substituted carbonyl group.

The term "halogen" as utilized in the instant specification denotes all form halogens, i.e., chlorine, bromine, iodine and fluorine, with chlorine and bromine being preferred. The terms "lower alkyl" and "lower alkenyl" denote both straight- and branched-chain groups containing 1 to 6 carbon atoms such as, for example, methyl, ethyl, isopropyl and 2-methylpropyl and vinyl, allyl and butenyl, respectively. The terms "lower alkoxy" and "lower alkenoxy" denote groups containing 1 to 6 carbon atoms such as, for example, methoxy, ethoxy and isopropoxy and vinyloxy and allyloxy, respectively. The lower alkanoyloxy groups preferably contain up to 6 carbon atoms such as, for example, acetoxy, propionyloxy, butyryloxy and the like.

The amino group as represented in the above formulae may be mono- or disubstituted by lower alkyl groups containing from 1 to 6 carbon atoms such as, for example, methylamino, diethylamino and isopropylamino. The alkanoyl portion of the lower alkanoylamido groups of the above formula can be derived from lower alkanecarboxylic acids having 1 to 6 carbon atoms such as, for example, acetic acid, propionic acid, pivalic acid and the like.

The terminology "nitrogen-containing heterocycle" as utilized herein denotes a 5- or 6-membered ring containing a nitrogen atom and which may contain an additional hetero atom selected from the group consisting of oxygen, nitrogen and sulfur. Examples of preferred groups in accordance with the invention include pyrrolidino, pyridino, piperidino, morpholino and thiomorpholino. The alkoxy portion of the alkoxymethyl and alkoxycarbonyl groups are preferably straight- or branched-chain groups containing from 1 to 6 carbon atoms such as, for example, methoxy, ethoxy or isopropoxy. The alkoxy portion of said groups, however, may also contain from 7 to 20 carbon atoms. Of this group the cetyloxy group is preferred.

The alkenoxycarbonyl and alkynoxycarbonyl groups in the above formula preferably contain 2 to 6 carbon atoms in the alkenoxy and the alkynoxy portions, respectively. Examples of suitable groups include alkyloxy and 2-propynyloxy. The alkanoyloxy portion of the alkanoyloxymethyl group of the above formula can be derived from lower alkanecarboxylic acids having from 1 to 20 carbons, preferably from 1 to 6 carbon atoms. Examples of suitable acids include acetic acid, propionic acid, pivalic acid, palmitic acid and stearic acid. The carbamoyl group of the above formula can be mono- or di-substituted by straight- or branched-chain lower alkyl groups. Examples of suitable preferred groups include methylcarbamoyl, dimethylcarbamoyl and diethylcarbamoyl. The nitrogen-containing heterocycle portion of the nitrogen-containing heterocycle-substituted carbonyl group is as defined above.

Preferred compounds of formula I in accordance with the invention include the following:

3,7-dimethyl-9-(2,6,6-trimethyl-cyclohex-1-en-1-yl)-nona-2,4,6-trien-1-oic acid methyl ester;
3,7-dimethyl-9-(2,6,6-trimethyl-cyclohex-1-en-1-yl)-nona-2,4,6-trien-1-oic acid;
3,7-dimethyl-9-(2,6,6-trimethyl-cyclohex-1-en-1-yl)-nona-2,4,6-trien-1-ol;
1-acetoxy-3,7-dimethyl-9-(2,6,6-trimethyl-cyclohex-1-en-1-yl)-nona-2,4,6-triene;
3,7-dimethyl-9-(2,3,6-trimethyl-phenyl)-nona-2,4,6-trien-1-oic acid;
3,7-dimethyl-9-(4-methoxy-2,3,6-trimethyl-phenyl)-nona-2,4,6-trien-1-oic acid methyl ester;
3,7-dimethyl-9-(3-chloro-2,4,6-trimethyl-phenyl)-nona-2,4,6-trien-1-oic acid;
3,7-dimethyl-9-(3-nitro-2,4,6-trimethyl-phenyl)-nona-2,4,6-trien-1-oic acid; and
3,7-dimethyl-9-(2,6-dimethyl-4-dimethylamino-phenyl)-nona-2,4,6-trien-1-oic acid methyl ester.

An especially preferred polyene compound of formula I hereinbefore is 3,7-dimethyl-9-(3-chloro-2,6-dimethyl-4-methoxy-phenyl)-nona-2,4,6-trien-1-oic acid methyl ester.

In accordance with the present invention, the novel polyene compounds of formula I are prepared by condensing a compound represented by the formula

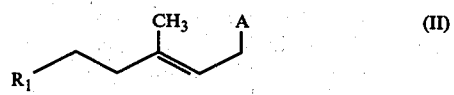

with a compound represented by the formula

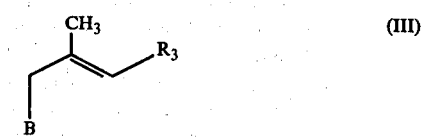

wherein one member of A and B is oxo and the other is a triarylphosphonium group represented by the formula $-P[Y]_3^+Z^-$ wherein Y is an aryl group, Z is an anion of an inorganic or organic acid or a dialkoxyphosphinoxy group represented by the formula

wherein X is alkoxy, $R_1$ is as given above and, wherein B is oxo, $R_3$ is selected from the group consisting of alkoxymethyl, dialkoxymethyl, alkanoyloxymethyl, alkoxycarbonyl, alkenoxycarbonyl and alkynoxycarbonyl, wherein B is triarylphosphonium or dialkoxyphosphinoxy, $R_3$ is selected from the group consisting of formyl, hydroxymethyl, alkoxymethyl, dialkoxymethyl, carboxyl, alkoxycarbonyl, alkenoxycarbonyl and alkynoxycarbonyl.

Wherein a carboxylic acid is obtained, it may be esterified or amidated. Wherein an ester is formed, it may, if desired, be hydrolyzed or amidated. Wherein either a carboxylic acid or ester are obtained, these may optionally be reduced to form the corresponding alcohol. Such alcohols may be etherified or esterified. The alcohol ester can also, if desired, be saponified. The alcohol or an ester thereof can further be oxidized to form the corresponding carboxylic acid.

The aryl groups represented by "Y" in the above formulae include all generally known aryl groups. Preferred groups include, for example, mononuclear groups such as phenyl, lower alkyl-substituted phenyl and lower alkoxysubstituted phenyl such as, for example, tolyl, xylyl, mesityl and p-methoxyphenyl. Preferred among the inorganic acid anions represented by "Z" in the above formulae are chlorine, bromide, iodide and hydrosulfate and, of the organic acid anions, the tosyloxy ion is preferred.

The alkoxy groups represented by "X" in the dialkoxyphosphinoxy group in the above formulae are preferably lower alkoxy groups containing from 1 to 6 carbon atoms. Especially preferred are methoxy and ethoxy groups.

The starting materials of formula II wherein $R_1$ is 2,6,6-trimethyl-cyclohex-1-en-1-yl are known. Those compounds wherein $R_1$ is a substituted phenyl group are novel and can be prepared, for example, by treating the corresponding substituted benzene conventionally with a formylating agent in the presence of a Lewis acid and condensing the resulting substituted benzaldehyde with acetone to yield a 4-(substituted-phenyl)-but-3-en-2-one. This product is conventionally reduced, e.g., with Raney-nickel and condensed with diethylphosphonoacetic acid ethyl ester to yield 3-methyl-5-(substituted-phenyl)-pent-2-en-1-oic acid ethyl ester. The ester is then reduced by conventional procedure using bis-(methoxy-ethenoxy)-sodium aluminum hydride to yield the corresponding 3-methyl-5-(substituted-phenyl)-pent-2-en-1-ol which is oxidized, e.g., by treatment with manganese dioxide in an organic solvent such as, for example, acetone, methylene chloride or the like to yield a compound of formula II wherein $R_1$ is substituted phenyl and A is oxo.

Starting materials of formula II wherein $R_1$ is substituted phenyl and A is triarylphosphonium or dialkoxyphosphinoxy can be prepared by conventionally halogenating the 3-methyl-5-(substituted-phenyl)-pent-2-en-1-ol described above, e.g., by treatment with a phosphorus trihalide or phosphorus pentahalide and reacting the product with a triarylphosphine or trialkylphosphite.

The starting materials of formula III above are known.

In accordance with the process provided by the present invention, the reaction of compounds of formulae II and III to give polyene compounds of formula I is carried out by a Wittig or Horner reaction.

According to the Wittig procedure, the starting materials are condensed together in the presence of an acid-binding agent, e.g., an alkali metal alcoholate such as sodium methylate or an alkylene oxide which may be alkyl-substituted, especially ethylene oxide or 1,2-butylene oxide. The reaction may be carried out, if desired, in a solvent, e.g., a chlorinated hydrocarbon such as methylene chloride, or dimethylformamide, at a temperature between room temperature and the boiling point of the condensation mixture.

According to the Horner procedure, the condensation is carried out with the aid of a base and preferably in the presence of an inert organic solvent such as, for example, using sodium hydride in benzene, toluene, dimethylformamide, tetrahydrofuran, dioxane or 1,2-dimethoxyethane, or using an alkali metal alcoholate in an alkanol such as sodium methylate in methanol at a temperature between 0° C. and the boiling point of the condensation mixture.

A carboxylic acid of formula I can be converted in a conventional manner, for example, by treatment with thionyl chloride into an acid chloride which can be converted into an amide by treatment with ammonia or into an ester by reaction with a suitable alkanol.

A carboxylic acid ester of formula I can be hydrolyzed to a carboxylic acid in a conventional manner such as, for example, by treatment with an alkali, preferably an aqueous-alcoholic solution of sodium hydroxide or potassium hydroxide at a temperature between room temperature and the boiling point of the mixture. The resulting carboxylic acid can then be amidated utilizing an acid halide as described above. Alternately, a carboxylic acid ester can be directly amidated as described hereinafter.

A carboxylic acid ester of formula I can be converted directly into the corresponding amide by treatment with lithium amide, preferably at room temperature.

A carboxylic acid or a carboxylic acid ester of formula I may be reduced to the corresponding alcohol in a conventional manner such as, for example, by treatment with a metal hydride or alkyl metal hydride in an inert solvent. Suitable hydrides include mixed metal hydrides such as lithium aluminum hydride and bis-[methoxy-ethylenoxy]-sodium aluminum hydride. Suitable inert solvents include, for example, ether, tetrahydrofuran and dioxane wherein lithium aluminum hydride is utilized and ether, hexane, benzene and toluene wherein diisobutyl-aluminum hydride or bis-[methyloxy-ethylenoxy]-sodium aluminum hydride are utilized.

An alcohol of formula I can be etherified with an alkyl halide such as, for example, ethyl iodide, in the presence of a base, preferably sodium hydride and in an organic solvent such as, for example, dioxane, tetrahydrofuran, 1,2-dimethoxyethane, dimethylformamide and the like, or in the presence of an alkali metal alcoholate in an alkanol and at a temperature between 0° C. and room temperature.

An alcohol of formula I can also be esterified by treatment with an alkanoyl halide or anhydride, preferably in the presence of a base such as, for example, pyridine or triethylamine at a temperature between room temperature and the boiling point of the mixture.

An alcohol ester can be saponified by conventional procedure such as previously described in connection with the carboxylic acid esters.

A diacetal of formula I can be saponified by conventional procedure such as, for example, by treatment with a proton donator in an inert solvent, e.g., hydrochloric acid in tetrahydrofuran.

An alcohol of formula I or an ester thereof can be oxidized to corresponding acid by conventional means such as, for example, silver (I) oxide and an alkali in water or an organic solvent miscible with water at a temperature between room temperature and the boiling point of the mixture.

The polyene compounds of formula I are useful in the topical and systemic prophylaxis and treatment of benign and malignant neoplasias and premalignant lesions. The tumor-inhibiting activity of the polyene compounds of the invention is significant. In the papilloma tests, tumors induced with dimethyl-benzanthracene and croton oil were shown to regress. The diameter of such papillomas in mice decreased by 54% within 2 weeks upon the intraperitoneal administration of 3,7-dimethyl-9-(4-methoxy-2,3,6-trimethyl-phenyl)-nona-2,4,6-trien-1-oic acid at a dosage of 400 mg/kg/week.

The polyene compounds of formula I are further useful in the topical and systemic treatment of acne, psoriasis and other dermatoses accompanied by an increased or pathologically altered cornification and for the treatment of inflammatory and allergic dermatological conditions. The compounds of formula I can also be utilized in the treatment of conditions of the mucous membranes characterized by inflammatory, degenerative or metaplastic alterations.

The compounds of formula I may be administered enterally, parenterally or topically. The dosages will vary according to mode of administration, the condition being treated and the requirements of the patient. For oral administration, from about 5 mg. to about 200 mg. of the compounds of formula I daily in one or more dosages are contemplated. A preferred oral dosage form is capsules containing from about 10 mg. to about 100 mg. of active ingredient. For topical administration, preferred dosage forms are solutions containing the active ingredient in from 0.01% by weight to about 0.3% by weight, preferably from about 0.02% by weight to about 0.1% by weight and ointments and creams containing from about 0.05% by weight to about 5% by weight, preferably from about 0.1% by weight to about 2.0% by weight active ingredient.

The toxicity of the polyene compounds of formula I is slight. For example, as is evident from the following Table, the acute toxicity ($LD_{50}$) in mice after intraperitoneal administration in rape oil of 3,7-dimethyl-9-(4-methoxy-2,3,6-trimethyl-phenyl)-nona-2,4,6-trien-1-oic acid is 1400 mg/kg.

Table

| Days Past Administration | Acute Toxicity | | |
|---|---|---|---|
| | $LD_{10}$ mg/kg | $LD_{50}$ mg/kg | $LD_{90}$ mg/kg |
| 1 | >4000 | >4000 | >4000 |
| 10 | 1200 | 1400 | 1800 |
| 20 | 1200 | 1400 | 1800 |

Wherein, in accordance with the present invention, the compounds of formula I are administered by either enteral or parenteral modes, suitable pharmaceutical dosage forms include tablets, capsules, dragees, syrups, suspensions, solutions, suppositories and the like for enteral administration. Parenteral dosage forms may be infusions or injectable solutions which can be injected intravenously or intramuscularly. These preparations can contain other medicinally active substances as well as inert binding agents, fillers, carriers or diluents. Additional additives such as flavoring agents, preservatives, stabilizers, emulsifying agents, buffers and the like may be added in accordance with accepted practices of pharmaceutical compounding. It is preferred to incorporate into the preparations herein described one or a mixture of antioxidants recognized as being suitable for such preparations such as, for example, N-methyl-γ-tocopherol-amine, tocopherols, butylated hydroxyanisole, butylated hydroxytoluene, ethoxyquin and the like. The carriers and diluents utilized may be organic or inorganic substances such as, for example, water, gelatin, lactose, starches, magnesium stearate, talc, gum arabic, polyalkyleneglycols and the like.

For topical administration, the polyene compounds of formula I are incorporated into ointments, tinctures, creams, solutions, lotions, sprays, suspensions and the like. Ointments, creams and solutions are preferred. These pharmaceutical preparations for topical administration can be prepared by mixing the polyene compounds, as the active ingredient, with non-toxic, inert solid or liquid carriers suitable for topical treatment in accordance with accepted pharmaceutical practices.

The following examples further illustrate the invention. All temperatures are in degrees Centigrade.

The following Examples illustrate the process provided by the present invention.

EXAMPLE 1

A total of 3.72 g. of sodium hydride was washed with low-boiling petroleum ether and, after the addition of 50 ml. of anhydrous benzene, treated with 25.05 g. of cis/trans-4-diethoxyphosphono-3-methyl-but-2-en-1-oic acid methyl ester in 200 ml. of benzene. The mixture was heated at 40°–45° for 6 hours, cooled to 15°–20° and, after the addition of 15.75 g. of trans-3-methyl-5-(2,6,6-trimethylcyclohex-1-en-yl)-pent-2-en-1-al in 50 ml. of benzene, stirred for 12 hours. The mixture was subsequently poured onto ice and extracted with ether. The ether extract was washed neutral with a saturated aqueous sodium chloride solution, dried over sodium sulfate and evaporated. The residual 2-cis/trans-3,7-dimethyl-9-(2,6,6-trimethyl-cyclohex-1-en-yl)-nona-2,4,6-trien-1-oic acid methyl ester was purified by adsorption on silica gel, eluant: methylene chloride/hexane (8:2) and separated into the 2-cis and 2-trans esters which can be converted into the free acids as described hereinafter:

44 Grams of all-trans-3,7-dimethyl-9-(2,6,6-trimethylcyclohex-1-en-1-yl)-nona-2,4,6-trien-1-oic acid methyl ester were introduced into 500 ml. of methanol. After the addition of 44 g. of potassium hydroxide in 50 ml. of water, the mixture was heated to boiling under reflux for 2.5 hours in an inert gas atmosphere. The solution obtained was acidified and extracted with ether. The ether extract was dried and evaporated. The residual all-trans-3,7-dimethyl-9-(2,6,6-trimethylcyclohex-1-en-1-yl)-nona-2,4,6-trien-1-oic acid melted at 149° after three recrystallizations from hexane/methylene chloride (9:1).

EXAMPLE 2

A total of 5.45 g. of 4-(4-methoxy-2,3,6-trimethyl-phenyl)-but-3-en-2-one were hydrogenated under normal conditions in 100 ml. of ethanol using 5 ml. of Raney-nickel in 50 ml. of ethanol. The hydrogenation was terminated after the uptake of the theoretical amount of hydrogen and the catalyst filtered off. The 4-(4-methoxy-2,3,6-trimethyl-phenyl)-butan-2-one remaining after evaporation of the filtrate melted at 87° after two recrystallizations from hexane.

30.6 Grams of sodium hydride were washed with low-boiling petroleum ether and, after the addition of 750 ml. of benzene, treated dropwise with 171.5 g. of diethoxyphosphono-acetic acid ethyl ester under an inert gas atmosphere without cooling thereby causing the internal temperature to rise to 35°. The mixture was stirred for 1 hour at about 30° and then treated with 141 g. of 4-(4-methoxy-2,3,6-trimethyl-phenyl)-butan-2-one in 400 ml. of benzene. The resulting mixture was stirred for 12 hours, then diluted with water and stirred for an additional 15 minutes. The organic phase was separated and the aqueous phase extracted with ether. The combined extracts were washed neutral with water, dried over sodium sulfate and evaporated. The residual 3-methyl-5-(4-methoxy-2,3,6-trimethyl-phenyl)-pent-2-en-1-oic acid ethyl ester melted at 45° after recrystallization from low-boiling petroleum ether.

25.3 Grams of the 3-methyl-5-(4-methoxy-2,3,6-trimethyl-phenyl)-pent-2-en-1-oic acid ethyl ester formed above were dissolved in 100 ml. of absolute ether. The resulting solution was cooled to 5° and, after the dropwise addition of a solution of 34 ml. of a 70% benzene solution of bis-(methoxy-ethylenoxy)sodium hydride in 50 ml. of absolute ether, stirred for 4 hours at 35°. The mixture was then cooled to 0° and treated dropwise with 300 ml. of 20% sodium hydroxide. The organic phase was separated, washed neutral, dried over sodium sulfate and evaporated. The residual trans-3-methyl-5-(4-methoxy-2,3,6-trimethylphenyl)-pent-2-en-1-ol melted at 80° after recrystallization from ethyl acetate.

16.2 Grams of 3-methyl-5-(4-methoxy-2,3,6-trimethyl-phenyl)-pent-2-en-1-ol in 350 ml. of methylene chloride were stirred, after the addition of 115.7 g. of manganese dioxide, for 15 hours at room temperature. The oxidizing agent was then separated and the filtrate obtained evaporated. The residual crude 3-methyl-5-(4-methoxy-2,3,6-trimethyl-phenyl)-pent-2-en-1-al melted at 66° after recrystallization from ethyl acetate.

A total of 22.4 g. of sodium hydride were washed with low-boiling petroleum ether and, after the addition of 800 ml. of benzene, treated dropwise at room temperature with 34 g. of 4-diethoxyphosphono-3-methyl-but-2-en-1-oic acid methyl ester. The mixture was stirred for 5 hours at 35°–45° and, after cooling to 5°–10°, treated dropwise with 96.7 g. of 3-methyl-5-(4-methoxy-2,3,6-trimethyl-phenyl)-pent-2-en-1-al. The mixture was heated to boiling under reflux for 12 hours, then cooled, diluted with water and extracted with ether. The ether extract was washed neutral, dried and evaporated. The residual oily cis/trans-3,7-dimethyl-9-(4-methoxy-2,3,6-trimethyl-phenyl)-nona-2,4,6-trien-1-oic acid methyl ester was purified by adsorption on silica gel, eluant: methylene chloride/hexane (8:2) and separated into the cis and trans forms.

40 Grams of all-trans-3,7-dimethyl-9-(4-methoxy-2,3,6-trimethyl-phenyl)-nona-2,4,6-trien-1-oic acid methyl ester were stirred, after the addition of 40 g. of potassium hydroxide in 400 ml. of methanol, for 15 hours at 50°. The mixture obtained was then diluted with water, acidified with concentrated hydrochloric acid and extracted with methylene chloride. The methylene chloride extract was washed with water, dried and evaporated. The residual all-trans-3,7-dimethyl-9-(4-methoxy-2,3,6-trimethyl-phenyl)-nona-2,4,6-trien-1-oic acid melted at 200°–201° after recrystallization from ethyl acetate.

EXAMPLE 3

A total of 42.5 g. of distilled ethyl acetoacetate are added slowly over a period of 30 minutes to a suspension of 15.7 g. of sodium hydride in 500 ml. of dimethoxyethane under an inert gas atmosphere. The mixture was then heated at reflux for 1 hour, cooled and added dropwise over a period of 30 minutes to a cooled (5°) solution of 72 g. of 2,6-dimethyl-3-chloro-4-methoxy-benzyl chloride in 300 ml. of dimethoxyethane. The resulting mixture was heated at reflux overnight. The mixture was then cooled, filtered through diatomaceous earth and washed with ether. The filtrate and the ether washings were washed neutral with saturated sodium chloride solution and dried. After evaporation of the solvent, there were obtained 102 g. of crude 3-carbethoxy-4-(3-chloro-4-methoxy-2,6-dimethyl-phenyl)-2-butanone which were dissolved in 500 ml. of 70% ethanol under an inert gas atmosphere. 100 Grams of potassium hydroxide were then added and the mixture is heated at reflux for 1 hour, cooled and acidified with concentrated hydrochloric acid. The mixture was again heated for 30 minutes in order to complete the decarboxylation, cooled and extracted with methylene chloride. The methylene chloride extracts were washed neutral with water, dried and the solvent evaporated. There was obtained 80 g. of crude crystals which were recrystallized from 400 ml. of hexane and 100 ml. of ethyl acetate to yield 56 g. of 4-(3-chloro-4-methoxy-2,6-dimethyl-phenyl)-2-butanone as colorless crystals, m.p. 106°.

40 Grams of triethylphosphonoacetate were slowly added at room temperature to a suspension of 7.2 g. of sodium hydride in 500 ml. of anhydrous benzene under an inert gas atmosphere. The mixture was then stirred at room temperature for 1 hour. The mixture was then cooled to 15° and treated over a period of 30 to 45 minutes with a solution of 36 g. of 4-(3-chloro-4-methoxy-2,6-dimethyl-phenyl)-2-butanone in 400 ml. of anhydrous benzene. The resulting mixture was stirred overnight. The cooled mixture was then poured into ice-water and extracted with ether. The organic phase was separated, washed neutral with saturated sodium chloride solution and dried over anhydrous sulfate. After evaporation of the solvent, there was obtained 62 g. of an oil which is purified by chromatography on silica gel to yield 25 g. of pure ethyl trans-3-methyl-5-(3-chloro-4-methoxy-2,6-dimethyl-phenyl)-2-pentenoate, m.p. 42°–44° after recrystallization from hexane.

A total of 37 ml. of a 70% solution of sodium dihydro-bis-(2-methoxyethoxy)aluminate in anhydrous ether was added over a period of 30 minutes under an inert gas atmosphere to a cooled (5°) solution of 31 g. of ethyl trans-3-methyl-5-(3-chloro-4-methoxy-2,6-dimethyl-phenyl)-2-pentenoate in 110 ml. of anhydrous ether. After completion of the addition, the mixture was heated at reflux for 3 hours. The solution was then cooled to 5° and cautiously treated with a 20% aqueous sodium hydroxide solution until two clear phases result. The organic layer was separated, washed neutral with saturated sodium chloride solution, dried over anhydrous sodium sulfate and the solvent evaporated. After recrystallization of the oily residue from ethyl acetate/hexane (1:2), there were obtained 25.3 g. of colorless crystals of trans-3-methyl-5-(3-chloro-4-methoxy-2,6-dimethyl-phenyl)-2-penten-1-ol, m.p. 72°–73°.

A mixture of 6.5 g. of trans-3-methyl-5-(3-chloro-4-methoxy-2,6-dimethyl-phenyl)-2-penten-1-ol formed above in 250 ml. of methylene chloride was stirred for 3.5 hours with 35 g. of activated maganese dioxide at room temperature under an inert gas atmosphere. After filtration and evaporation of the solvent, there were obtained 5.1 g. of crude trans-3-methyl-5-(3-chloro-4-methoxy-2,6-dimethyl-phenyl)-2-pentenal, m.p. 96°–98° after recrystallization from ethyl acetate/hexane.

A solution of 20 g. of dimethyl 2-methyl-3-carbomethoxy-2-propenyl phosphonate in 75 ml. of tetrahydrofuran was added at 10° under an inert gas atmosphere to a suspension of 3.65 g. of sodium hydride in 80 ml. of anhydrous tetrahydrofuran. The mixture was stirred for 30 minutes at constant temperature and a solution of 16 g. of trans-3-methyl-5-(3-chloro-4-methoxy-2,6-dimethyl-phenyl)-2-pentenal in 75 ml. of tetrahydrofuran added thereto. The resulting mixture was stirred for a further 1 hour at room temperature and then poured into ice-water. The organic phase was separated, concentrated, diluted with ether, washed neutral with saturated sodium chloride solution and then dried over anhydrous sodium sulfate. After evaporation of the solvent, there was obtained crude all-trans-3,7-dimethyl-9-(3-chloro-2,6-dimethyl-4-methoxy-phenyl)-nona-2,4,6-trien-1-oic acid methyl ester which was purified by fractional crystallization from hexane/ethyl acetate (3:1). After three recrystallizations, there were obtained 1.75 g. of colorless crystals, m.p. 122°–123°.

EXAMPLE 4

A total of 91.5 g. of a 10% aqueous sodium hydroxide solution was added dropwise to a cold (0°) mixture of 32.6 g. of 4-dimethyl-amino-2,6-dimethylbenzaldehyde, 440 ml. of acetone and 190 ml. of water. After completion of the addition, the stirring was continued for 3 days. The acetone was then evaporated and the aqueous solution extracted thrice with 3 ml. portions of ether. The organic layer was washed with sodium chloride solution and dried. After evaporation of the solvent, there were obtained 51 g. of a crude product which was crystallized from 550 ml. of hexane to yield 34.4 g. of 4-(2,6-dimethyl-4-dimethylamino-phenyl)-buten-2-one as yellow crystals, m.p. 93°–95°.

A mixture of 20 g. of 4-(2,6-dimethyl-4-dimethylamino-phenyl)-buten-2-one, 10 ml. of Raney-nickel and 800 ml. of ethanol was stirred under atmospheric pressure with the addition of hydrogen until the theoretical amount of hydrogen (ca 2.3 liters) was taken up. The catalyst was then filtered off and the solvent removed on a rotary evaporator. After purification by recrystallization from hexane, there was obtained 16 g. of 4-(2,6-dimethyl-4-dimethylamino-phenyl)butan-2-one, m.p. 42°–53°. Analytically pure sample melted at 57°–58°.

A total of 2.7 g. of triethylphosphonoacetate was added under an inert gas atmosphere to a cold (15°) suspension of 0.48 g. of sodium hydride in 5 ml. of benzene. After completion of the addition, the mixture was stirred for 1 hour and then treated dropwise with a solution of 2.19 g. of 4-(2,6-dimethyl-4-dimethylamino-phenyl)-butan-2-one in 6 ml. of benzene. The mixture was then heated at 60° for 3 hours, cooled, diluted with ether and washed neutral with saturated sodium chloride solution. The organic layer was separated, dried over sodium sulfate and concentrated on a rotary evaporator to yield 2.8 g. of an oil which was chromatographed on 100 g. of silica gel. Elution with ethyl acetate/hexane (1:9) gave 2.5 g. of trans-3-methyl-5-(2,6-dimethyl-4-dimethylamino-phenyl)-pent-2-en-1-oic acid ethyl ester as a light yellow oil of boiling point 182°–187°/0.15 mm Hg.

5.5 Milliters of a 70% by weight solution of sodium dihydro-bis-(2-methoxyethoxy)-aluminate in benzene were added dropwise to a cold (0°) solution of 2.89 g. of trans-3-methyl-5-(2,6-dimethyl-4-dimethylamino-phenyl)-pent-2-en-1-oic acid ethyl ester in 25 ml. of anhydrous ether. The mixture was stirred and slowly brought to room temperature over a period of 5.5 hours, then again cooled and treated dropwise with 30 ml. of a 20% aqueous sodium hydroxide solution. The stirring was continued for a further 20 minutes. The organic layer was separated, washed neutral with saturated sodium chloride solution and dried over sodium sulfate. Evaporation of the solvent gave 2.3 g. of an oil which solidified. The solid was recrystallized from hexane to yield 1.6 g. of trans-3-methyl-5-(2,6-dimethyl-4-dimethylamino-phenyl)-2-penten-1-ol, m.p. 73°–75° after recrystallizations from hexane.

A mixture of 14.65 g. of the trans-3-methyl-5-(2,6-dimethyl-4-dimethylamino-phenyl)-2-penten-1-ol formed above, 43.5 g. of silver carbonate on calcium carbonate and 500 ml. of petroleum ether (boiling range 60°–90°) was heated at reflux for 7.5 hours, the water which separated being collected in a Dean-Stark trap. The mixture was then cooled, filtered and the residue washed with petroleum ether. Evaporation of the filtrate gave 13.8 g. of an oil which was chromatographed on 400 g. of silica gel. By elution with ethyl acetate/hexane (1:19) and then with ethyl acetate/hexane (1:9) there was obtained 8.4 g. of trans-3-methyl-5-(2,6-dimethyl-4-dimethylamino-phenyl)-2-penten-1-al as a yellow oil of boiling point 140°–141°/0.1 mm Hg.

A total of 1.38 g. of 4-diethoxyphosphono-3-methyl-but-en-1-oic acid methyl ester in 10 ml. of benzene was added under an inert gas atmosphere to a suspension, cooled to 15°, of 0.2 g. of sodium hydride in 5 ml. of benzene. After stirring for 1 hour, there was rapidly added a solution of 1 g. of trans-3-methyl-5-(2,6-dimethyl-4-dimethylamino-phenyl)-2-penten-1-al in 5 ml. of benzene. The mixture was stirred at room temperature overnight, then diluted with water and the organic phase separated. The aqueous phase was extracted twice with ether and the combined organic extracts washed neutral with saturated sodium chloride solution and dried. The solvent was removed on a rotary evaporator to yield 1.9 g. of a yellow oil which is chromatographed on 90 g. of silica gel. Elution with ethyl acetate in benzene (gradual increase of 2% to 4% ethyl acetate) yielded 0.15 g. of trans-3,7-dimethyl-9-(2,6-dimethyl-4-dimethylamino-phenyl)-nona-2,4,6-trien-1-oic acid methyl ester. An analytically pure sample melted at 110°–111° after three recrystallizations from pentane.

EXAMPLE 5

Soft gelatin capsules were filled with the following composition:

| Ingredient | Amount in mg. |
| --- | --- |
| 3,7-Dimethyl-9-(4-methoxy-2,3,6-trimethyl-phenyl)-nona-2,4,6-trien-1-oic acid | 10.0 |

| Ingredient | Amount in mg. |
|---|---|
| Wax mixture | 41.5 |
| Vegetable Oil | 98.0 |
| Trisodium salt of ethylenediamine tetraacetic acid | 0.5 |
| | 150.0 |

An individual capsule weighs 150 mg. and contains 10 mg. of active ingredient.

EXAMPLE 6

An ointment containing 0.3% active ingredient was prepared in a conventional manner from the following composition:

| Ingredient | Amount in Grams |
|---|---|
| 3,7-Dimethyl-9-(4-methoxy-2,3,6-trimethyl-phenyl)-nona-2,4,6-trien-1-oic acid | 0.3 |
| Cetyl alcohol | 2.7 |
| Lanolin | 6.0 |
| White petroleum jelly | 15.0 |
| Distilled water q.s. ad | 100.0 |

EXAMPLE 7

A water/fat emulsion containing 0.3% active ingredient was prepared by conventional procedure from the following composition:

| Ingredient | Amount in Grams |
|---|---|
| 3,7-Dimethyl-9-(4-methoxy-2,3,6-trimethyl-phenyl)-nona-2,4,6-trien-1-oic acid | 0.3 |
| Magnesium stearate | 2.0 |
| Perhydrosqualene | 13.0 |
| Distilled water q.s. ad | 100.0 |

I claim:

1. A compound selected from compounds represented by the formula

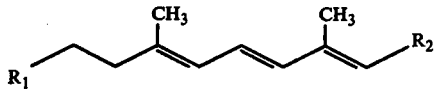

wherein $R_1$ is a 2,6,6-trimethyl-cyclohex-1-en-1-yl group or a phenyl group substituted in positions 2 and 6 by a member selected from the group consisting of halogen, lower alkyl and lower alkoxy and in at least one of positions 3, 4 and 5 by a member selected from the group consisting of halogen, hydroxy, lower alkyl, lower alkenyl, lower alkoxy, lower alkenoxy, lower alkanoyloxy, nitro, amino, mono(lower alkyl)amino, di(lower alkyl)amino, lower alkanoylamido, and a nitrogen-containing heterocyclic group and $R_2$ is selected from the group consisting of carboxyl and alkoxycarbonyl.

2. A compound in accordance with claim 1 wherein said compound is 3,7-dimethyl-9-(2,6,6-trimethyl-cyclohex-1-en-1-yl)-nona-2,4,6-trien-1-oic acid.

3. A compound in accordance with claim 1 wherein said compound is 3,7-dimethyl-9-(4-methoxy-2,3,6-trimethyl-phenyl)-nona-2,4,6-trien-1-oic acid.

4. A compound in accordance with claim 1 wherein said compound is 3,7-dimethyl-9-(2,6-dimethyl-4-dimethylamino-phenyl)-nona-2,4,6-trien-1-oic acid methyl ester.

5. A compound in accordance with claim 1 wherein said compound is 3,7-dimethyl-9-(3-chloro-2,6-dimethyl-4-methoxy-phenyl)-nona-2,4,6-trien-1-oic acid methyl ester.

* * * * *